(12) United States Patent
Robinson et al.

(10) Patent No.: US 11,083,884 B2
(45) Date of Patent: Aug. 10, 2021

(54) APPARATUS FOR NEGATIVE-PRESSURE THERAPY AND IRRIGATION

(71) Applicant: KCI Licensing, Inc., San Antonio, TX (US)

(72) Inventors: Timothy Mark Robinson, Shillingstone (GB); Christopher Brian Locke, Bournemouth (GB); James A. Luckemeyer, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 412 days.

(21) Appl. No.: 15/580,756

(22) PCT Filed: Jun. 27, 2016

(86) PCT No.: PCT/US2016/039610
§ 371 (c)(1),
(2) Date: Dec. 8, 2017

(87) PCT Pub. No.: WO2017/003938
PCT Pub. Date: Jan. 5, 2017

(65) Prior Publication Data
US 2018/0140822 A1 May 24, 2018

Related U.S. Application Data

(60) Provisional application No. 62/186,093, filed on Jun. 29, 2015.

(51) Int. Cl.
*A61M 39/22* (2006.01)
*A61M 1/00* (2006.01)
(Continued)

(52) U.S. Cl.
CPC .......... *A61M 39/22* (2013.01); *A61M 1/0058* (2013.01); *A61M 1/85* (2021.05);
(Continued)

(58) Field of Classification Search
CPC ............ A61M 39/22; A61M 2039/226; A61M 39/227; A61M 2039/2473;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

(Continued)

*Primary Examiner* — Catharine L Anderson
*Assistant Examiner* — Arjuna P Chatrathi (57) ABSTRACT

Systems, methods, and apparatuses for irrigating a tissue site are described. The system can include a tissue interface and a sealing member configured to be placed over the tissue site to form a sealed space, and a negative-pressure source fluidly coupled to the sealed space. The system includes an irrigation valve having a housing, a piston disposed in the housing, a fluid inlet to fluidly couple a fluid inlet chamber to a fluid source, and a fluid outlet to fluidly couple a fluid outlet chamber to the sealed space. A piston passage extends through the piston and fluidly couples the fluid inlet chamber and the fluid outlet chamber, and a biasing member is coupled to the piston to bias the irrigation valve to a closed position. The negative-pressure source is configured to (Continued)

move the piston between the closed position and an open position to draw fluid to the sealed space.

40 Claims, 3 Drawing Sheets

(51) Int. Cl.
    *F16K 31/122*      (2006.01)
    *F16K 31/363*      (2006.01)
    *F16K 1/38*      (2006.01)
    *A61M 3/02*      (2006.01)
    *A61F 13/02*      (2006.01)

(52) U.S. Cl.
    CPC ............ *A61M 1/90* (2021.05); *A61M 3/0262* (2013.01); *A61M 39/227* (2013.01); *A61M 39/228* (2013.01); *F16K 1/38* (2013.01); *F16K 31/1221* (2013.01); *F16K 31/1226* (2013.01); *F16K 31/363* (2013.01); *A61F 13/0206* (2013.01); *A61M 1/0062* (2013.01); *A61M 2039/226* (2013.01); *Y10S 137/907* (2013.01)

(58) Field of Classification Search
    CPC ... A61M 2039/2486; A61M 2039/0009; Y10S 137/907
    See application file for complete search history.

(56) References Cited

U.S. PATENT DOCUMENTS

| | | | |
|---|---|---|---|
| 2,632,443 A | | 3/1953 | Lesher |
| 2,682,873 A | | 7/1954 | Evans et al. |
| 2,910,763 A | | 11/1959 | Lauterbach |
| 2,969,057 A | | 1/1961 | Simmons |
| 3,066,672 A | | 12/1962 | Crosby, Jr. et al. |
| 3,122,126 A | * | 2/1964 | *Yamada ............ B01F 3/04744 119/225 |
| 3,122,162 A | * | 2/1964 | *Sands .................... F16K 17/30 137/498 |
| 3,367,332 A | | 2/1968 | Groves |
| 3,520,300 A | | 7/1970 | Flower, Jr. |
| 3,568,675 A | | 3/1971 | Harvey |
| 3,626,959 A | * | 12/1971 | Santomieri ....... A61M 5/16881 137/1 |
| 3,648,692 A | | 3/1972 | Wheeler |
| 3,682,180 A | | 8/1972 | McFarlane |
| 3,727,629 A | * | 4/1973 | Gifford ................... F16K 31/22 137/205 |
| 3,746,036 A | * | 7/1973 | Du Bois .................. F16K 24/00 137/496 |
| 3,770,009 A | * | 11/1973 | Miller .................... F16K 15/026 137/543.19 |
| 3,826,254 A | | 7/1974 | Mellor |
| 3,943,969 A | * | 3/1976 | Rubin .................... A01G 25/16 137/538 |
| 4,080,970 A | | 3/1978 | Miller |
| 4,096,853 A | | 6/1978 | Weigand |
| 4,139,004 A | | 2/1979 | Gonzalez, Jr. |
| 4,165,748 A | | 8/1979 | Johnson |
| 4,177,947 A | * | 12/1979 | Menzel ................. B05B 1/3026 138/45 |
| 4,184,510 A | | 1/1980 | Murry et al. |
| 4,233,969 A | | 11/1980 | Lock et al. |
| 4,245,630 A | | 1/1981 | Lloyd et al. |
| 4,256,109 A | | 3/1981 | Nichols |
| 4,261,363 A | | 4/1981 | Russo |
| 4,275,721 A | | 6/1981 | Olson |
| 4,284,079 A | | 8/1981 | Adair |
| 4,297,995 A | | 11/1981 | Golub |
| 4,315,506 A | * | 2/1982 | Kayser ................ A61M 1/0037 251/63 |
| 4,317,473 A | * | 3/1982 | Gaydos ................ A61M 5/1411 138/45 |
| 4,333,468 A | | 6/1982 | Geist |
| 4,373,519 A | | 2/1983 | Errede et al. |
| 4,382,441 A | | 5/1983 | Svedman |
| 4,392,853 A | | 7/1983 | Muto |
| 4,392,858 A | | 7/1983 | George et al. |
| 4,419,097 A | | 12/1983 | Rowland |
| 4,465,485 A | | 8/1984 | Kashmer et al. |
| 4,475,909 A | | 10/1984 | Eisenberg |
| 4,480,638 A | | 11/1984 | Schmid |
| 4,525,166 A | | 6/1985 | Leclerc |
| 4,525,374 A | | 6/1985 | Vaillancourt |
| 4,540,412 A | | 9/1985 | Van Overloop |
| 4,543,100 A | | 9/1985 | Brodsky |
| 4,548,202 A | | 10/1985 | Duncan |
| 4,551,139 A | | 11/1985 | Plaas et al. |
| 4,569,348 A | | 2/1986 | Hasslinger |
| 4,605,399 A | | 8/1986 | Weston et al. |
| 4,608,041 A | | 8/1986 | Nielsen |
| 4,640,688 A | | 2/1987 | Hauser |
| 4,655,754 A | | 4/1987 | Richmond et al. |
| 4,664,662 A | | 5/1987 | Webster |
| 4,710,165 A | | 12/1987 | McNeil et al. |
| 4,733,659 A | | 3/1988 | Edenbaum et al. |
| 4,743,232 A | | 5/1988 | Kruger |
| 4,758,220 A | | 7/1988 | Sundblom et al. |
| 4,787,888 A | | 11/1988 | Fox |
| 4,826,494 A | | 5/1989 | Richmond et al. |
| 4,838,883 A | | 6/1989 | Matsuura |
| 4,840,187 A | | 6/1989 | Brazier |
| 4,863,449 A | | 9/1989 | Therriault et al. |
| 4,872,450 A | | 10/1989 | Austad |
| 4,878,901 A | | 11/1989 | Sachse |
| 4,897,081 A | | 1/1990 | Poirier et al. |
| 4,906,233 A | | 3/1990 | Moriuchi et al. |
| 4,906,240 A | | 3/1990 | Reed et al. |
| 4,919,654 A | | 4/1990 | Kalt |
| 4,941,882 A | | 7/1990 | Ward et al. |
| 4,953,565 A | | 9/1990 | Tachibana et al. |
| 4,969,880 A | | 11/1990 | Zamierowski |
| 4,985,019 A | | 1/1991 | Michelson |
| 5,037,397 A | | 8/1991 | Kalt et al. |
| 5,054,518 A | * | 10/1991 | Rancani .............. A61M 27/006 137/516.27 |
| 5,086,170 A | | 2/1992 | Luheshi et al. |
| 5,092,858 A | | 3/1992 | Benson et al. |
| 5,100,396 A | | 3/1992 | Zamierowski |
| 5,134,994 A | | 8/1992 | Say |
| 5,149,331 A | | 9/1992 | Ferdman et al. |
| 5,167,613 A | | 12/1992 | Karami et al. |
| 5,176,663 A | | 1/1993 | Svedman et al. |
| 5,215,522 A | | 6/1993 | Page et al. |
| 5,232,453 A | | 8/1993 | Plass et al. |
| 5,261,893 A | | 11/1993 | Zamierowski |
| 5,278,100 A | | 1/1994 | Doan et al. |
| 5,279,550 A | | 1/1994 | Habib et al. |
| 5,298,015 A | | 3/1994 | Komatsuzaki et al. |
| 5,342,376 A | | 8/1994 | Ruff |
| 5,344,415 A | | 9/1994 | DeBusk et al. |
| 5,358,494 A | | 10/1994 | Svedman |
| 5,437,622 A | | 8/1995 | Carion |
| 5,437,651 A | | 8/1995 | Todd et al. |
| 5,527,293 A | | 6/1996 | Zamierowski |
| 5,549,584 A | | 8/1996 | Gross |
| 5,556,375 A | | 9/1996 | Ewall |
| 5,607,388 A | | 3/1997 | Ewall |
| 5,636,643 A | | 6/1997 | Argenta et al. |
| 5,645,081 A | | 7/1997 | Argenta et al. |
| 5,826,621 A | * | 10/1998 | Jemmott ............. A61M 39/281 137/853 |
| 5,931,168 A | * | 8/1999 | Abercrombie ......... A61Q 5/065 132/208 |
| 6,071,267 A | | 6/2000 | Zamierowski |
| 6,135,116 A | | 10/2000 | Vogel et al. |
| 6,241,747 B1 | | 6/2001 | Ruff |
| 6,287,316 B1 | | 9/2001 | Agarwal et al. |
| 6,345,623 B1 | | 2/2002 | Heaton et al. |
| 6,488,643 B1 | | 12/2002 | Tumey et al. |
| 6,493,568 B1 | | 12/2002 | Bell et al. |
| 6,553,998 B2 | | 4/2003 | Heaton et al. |

(56) References Cited

U.S. PATENT DOCUMENTS

| | | | |
|---|---|---|---|
| 6,814,079 | B2 | 11/2004 | Heaton et al. |
| 7,846,141 | B2 | 12/2010 | Weston |
| 8,057,411 | B2 | 11/2011 | Warlick et al. |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,869,826 | B2 * | 10/2014 | Chappel ............... G05D 7/0133 137/504 |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 9,739,387 | B2 * | 8/2017 | Kristoffersen .......... F16K 1/307 |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2002/0189684 | A1 * | 12/2002 | Williamson .......... A61J 7/0053 137/510 |
| 2009/0054855 | A1 * | 2/2009 | Blott ................... A61M 1/0088 604/290 |
| 2014/0163491 | A1 | 6/2014 | Schuessler et al. |
| 2014/0360599 | A1 * | 12/2014 | Kristoffersen .......... F16K 1/307 137/488 |
| 2015/0080788 | A1 | 3/2015 | Blott et al. |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2166424 A1 | 3/2010 |
| ES | 2354472 T3 | 3/2011 |
| GB | 692578 A | 6/1953 |
| GB | 1077174 A | 7/1967 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2010031401 A1 | 3/2010 |
| WO | 2010075178 A2 | 7/2010 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp: 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al: "Closed Wound Suction Drainage", The Journal of Foot Surgery, vol. 24, No. 1, 1985, pp. 76-81.

Arnljots, Björn et al: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems (56) References Cited

OTHER PUBLICATIONS in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinoví?, V. ?uki?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax,"Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

Extended European Search Report for Corresponding Application No. 182065979, dated Feb. 4, 2019.

Chinese First Office Action for Corresponding Application No. 2016800480415, dated Feb. 3, 2020.

* cited by examiner

APPARATUS FOR NEGATIVE-PRESSURE THERAPY AND IRRIGATION

RELATED APPLICATIONS

This present invention is the National Stage of International Application No. PCT/US2016/039610, entitled "Apparatus for Negative-Pressure Therapy and Irrigation," filed Jun. 27, 2016 and claims the benefit of U.S. Provisional Patent Application No. 62/186,093, entitled "Apparatus for Negative-Pressure Therapy and Irrigation," filed Jun. 29, 2015, all of which are incorporated herein by reference for all purposes.

TECHNICAL FIELD

The invention set forth in the appended claims relates generally to tissue treatment systems and more particularly, but without limitation, to an apparatus for negative-pressure therapy and irrigation.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively.

While the clinical benefits of negative-pressure therapy and irrigation are widely known, the cost and complexity of negative-pressure therapy and irrigation therapy can be a limiting factor in its application, and the development and operation of negative-pressure systems, components, and processes and irrigation therapy systems, components, and processes continues to present significant challenges to manufacturers, healthcare providers, and patients.

BRIEF SUMMARY

New and useful systems, apparatuses, and methods for irrigating a tissue site in a negative-pressure therapy environment are set forth in the appended claims. Illustrative embodiments are also provided to enable a person skilled in the art to make and use the claimed subject matter. For example, a system for irrigating a tissue site is described. The system may include a tissue interface configured to be placed adjacent to the tissues site and a sealing member configured to be placed over the tissue interface to form a sealed space. The system may include negative-pressure source configured to be fluidly coupled to the sealed space. The system may also include an irrigation valve having a housing and a piston disposed in the housing. The piston may form a fluid inlet chamber and a fluid outlet chamber. The housing may have a fluid inlet that may be coupled to the housing and configured to fluidly couple the fluid inlet chamber to a fluid source, and a fluid outlet that may be coupled to the housing and configured to fluidly couple the fluid outlet chamber to the sealed space. A piston passage may extend through the piston and fluidly coupling the fluid inlet chamber and the fluid outlet chamber. A biasing member may be coupled to the piston to bias the irrigation valve to a closed position. The negative-pressure source is configured to move the piston between the closed position and an open position to draw fluid to the sealed space.

In another embodiment, an irrigation valve is described. The irrigation valve may include a valve body having a valve inlet and a valve outlet. The valve body may form a chamber having a plunger positioned in the chamber to form an inlet chamber in fluid communication with the valve inlet and an outlet chamber in fluid communication with the valve outlet. A bore may extend through the plunger and be in fluid communication with the inlet chamber and the outlet chamber. A spring may be positioned to bias the plunger away from the valve outlet to a closed position.

In yet another embodiment, a method for controlling irrigation of a tissue site is described. A tissue interface may be placed adjacent to the tissue site, and the tissue interface and the tissue site may be covered to form a sealed space. An irrigation valve may be fluidly coupled to the sealed space and a fluid source may be fluidly coupled to the irrigation valve. Negative pressure may be supplied to the irrigation valve through the tissue interface to open a fluid inlet of the irrigation valve and draw irrigation fluid to the tissue site through a fluid outlet of the irrigation valve.

In still another embodiment, a method for operating an irrigation valve is described. A fluid source may be fluidly coupled to a fluid inlet of the irrigation valve and a negative-pressure source may be fluidly coupled to a fluid outlet of the irrigation valve. Negative pressure may be supplied from the negative-pressure source to the fluid outlet of the irrigation valve. The negative pressure may draw a piston of the irrigation valve toward the fluid outlet to open a fluid inlet of the irrigation valve and may draw fluid through a passage of the piston and the fluid outlet of the irrigation valve.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
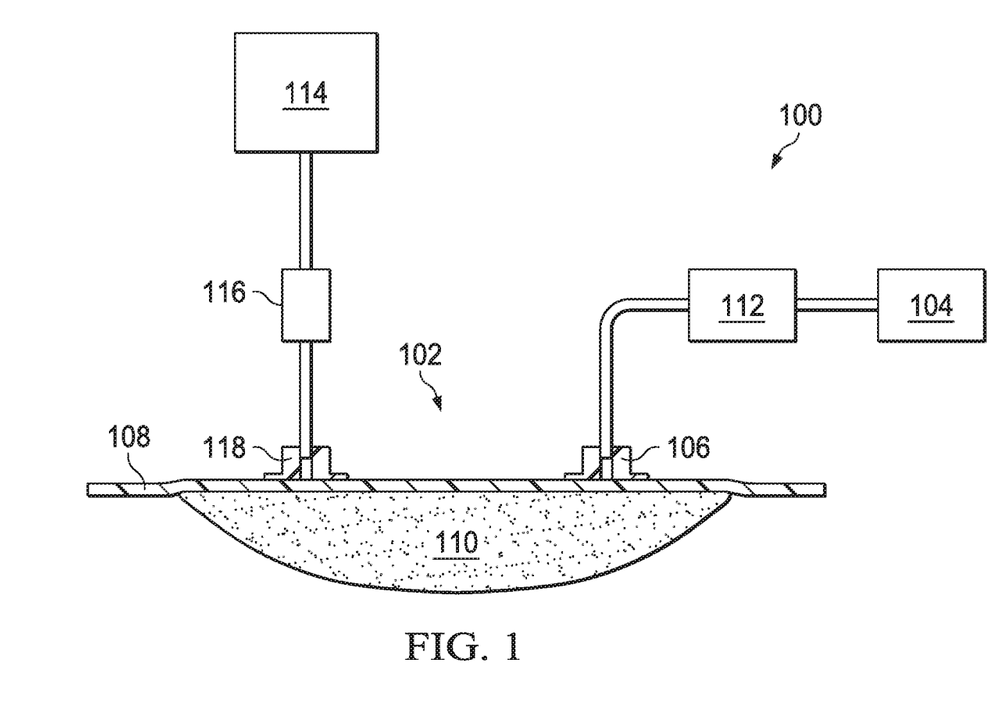
FIG. 1 is a functional block diagram of an example embodiment of a therapy system 100 that can irrigate a tissue site in accordance with this specification.

FIG. 1 is a simplified functional block diagram of an example embodiment of a therapy system 100 that can provide negative-pressure therapy and irrigation to a tissue site in accordance with this specification. The therapy system 100 may include a dressing and a negative-pressure source. For example, a dressing 102 may be fluidly coupled to a negative-pressure source 104, as illustrated in FIG. 1. In some embodiments, the negative-pressure source 104 may be fluidly coupled to the dressing 102 by a fluid interface, such as a connector 106. A dressing generally may include a cover and a tissue interface. The dressing 102, for example, can include a cover 108, and a tissue interface 110. The therapy system 100 may also include a fluid container, such as a container 112, coupled to the dressing 102 and to the negative-pressure source 104.

In some embodiments, the therapy system 100 may also provide irrigation of the tissue site. In some embodiments, the therapy system 100 may include a fluid source and an irrigation valve. For example, the therapy system 100 may include a fluid source 114 fluidly coupled to an irrigation valve 116. The irrigation valve 116 may be fluidly coupled to the dressing 102 with a fluid interface, such as a connector 118.

In general, components of the therapy system 100 may be coupled directly or indirectly. For example, the negative-pressure source 104 may be directly coupled to the container 112 and indirectly coupled to the dressing 102 through the container 112. Components may be fluidly coupled to each other to provide a path for transferring fluids (i.e., liquid and/or gas) between the components.

In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts.

In operation, the tissue interface 110 may be placed within, over, on, or otherwise proximate to a tissue site. The cover 108 may be placed over the tissue interface 110 and sealed to tissue near the tissue site. For example, the cover 108 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 110 in the sealed therapeutic environment can induce macrostrain and microstrain in the tissue site, as well as remove exudates and other fluids from the tissue site, which can be collected in container 112 and disposed of properly.

The fluid mechanics of using a negative-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies a position in a fluid path relatively closer to a negative-pressure source, and conversely, the term "upstream" implies a position relatively further away from a negative-pressure source. Similarly, it may be convenient to describe certain features in terms of fluid "inlet" or "outlet" in such a frame of reference. This orientation is generally presumed for purposes of describing various features and components of therapy systems herein. However, the fluid path may also be reversed in some applications (such as by substituting a positive-pressure source for a negative-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as sensors, processing units, alarm indicators, memory, databases, software, display devices, or user interfaces that further facilitate negative-pressure therapy. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

The tissue interface 110 can be generally adapted to contact a tissue site. The tissue interface 110 may be partially or fully in contact with the tissue site. If the tissue site is a wound, for example, the tissue interface 110 may partially or completely fill the wound, or may be placed over the wound. The tissue interface 110 may take many forms, and may have many sizes, shapes, or thicknesses depending on a variety of factors, such as the type of treatment being implemented or the nature and size of a tissue site. For example, the size and shape of the tissue interface 110 may be adapted to the contours of deep and irregular shaped tissue sites.

In some embodiments, the tissue interface 110 may be a manifold. A "manifold" in this context generally includes any substance or structure providing a plurality of pathways adapted to collect or distribute fluid across a tissue site under negative pressure. For example, a manifold may be adapted to receive negative pressure from a source and distribute the negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

In some illustrative embodiments, the pathways of a manifold may be channels interconnected to improve distribution or collection of fluids across a tissue site. For example, cellular foam, open-cell foam, reticulated foam, porous tissue collections, and other porous material such as gauze or felted mat generally include pores, edges, and/or walls adapted to form interconnected fluid pathways. Liquids, gels, and other foams may also include or be cured to include apertures and flow channels. In some illustrative embodiments, a manifold may be a porous foam material having interconnected cells or pores adapted to uniformly (or quasi-uniformly) distribute negative pressure to a tissue site. The foam material may be either hydrophobic or hydrophilic. In one non-limiting example, a manifold may be an open-cell, reticulated polyurethane foam such as GranuFoam® dressing available from Kinetic Concepts, Inc. of San Antonio, Tex.

In an example in which the tissue interface 110 may be made from a hydrophilic material, the tissue interface 110 may also wick fluid away from a tissue site, while continuing to distribute negative pressure to the tissue site. The wicking properties of the tissue interface 110 may draw fluid away from a tissue site by capillary flow or other wicking mechanisms. An example of a hydrophilic foam is a polyvinyl alcohol, open-cell foam such as V.A.C. WhiteFoam® dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 110 may further promote granulation at a tissue site when pressure within the sealed therapeutic environment is reduced. For example, any or all of the surfaces of the tissue interface 110 may have an uneven, coarse, or jagged profile that can induce microstrains and stresses at a tissue site if negative pressure is applied through the tissue interface 110.

In some embodiments, the tissue interface 110 may be constructed from bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones. The tissue interface 110 may further serve as a scaffold for new cell-growth, or a scaffold material may be used in conjunction with the tissue interface 110 to promote cell-growth. A scaffold is generally a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

In some embodiments, a sealing member, such as the cover 108 may provide a bacterial barrier and protection from physical trauma. The cover 108 may also be constructed from a material that can reduce evaporative losses and provide a fluid seal between two components or two environments, such as between a therapeutic environment and a local external environment. The cover 108 may be, for example, an elastomeric film or membrane that can provide a seal adequate to maintain a negative pressure at a tissue site for a given negative-pressure source. In some example embodiments, the cover 108 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 108 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 108 may be coated with an acrylic adhesive having a coating weight between 25-65 grams per square member (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

In some embodiments, the dressing 102 may also include a fluid interface, such as the connector 106, configured to fluidly couple the negative-pressure source 104 to the sealed therapeutic environment formed by the cover 108. In some embodiments, the fluid interface may include a flange portion that couples to the cover 108 and a portion that fluidly couples to a tube. In one exemplary embodiment, the fluid interface may be a T.R.A.C.® Pad or Sensa T.R.A.C.® Pad available from Kinetic Concepts, Inc. of San Antonio, Tex. In other exemplary embodiments, a tube may be inserted through the cover 108. Such a fluid interface can allow negative pressure to be delivered to the sealed therapeutic environment. For example, a fluid interface can provide a fluid conductor through the cover 108 to the tissue interface 110. In some embodiments, a fluid interface can also provide more than one fluid path through the cover 108 or merge more than fluid conductor into a single fluid path.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The fluid source 114 is representative of a container, canister, pouch, or other fluid storage component, which can be used to manage an irrigation fluid to be provided to a tissue site. In some embodiments, the fluid source 114 may be an intravenous (IV) bag suspended from an intravenous pole. In other embodiments, the fluid source 114 may be another fluid storage device positioned proximate to a tissue site. In some embodiments, the fluid source 114 may be positioned vertically above a tissue site. In other embodiments, the fluid source 114 may be positioned vertically level or below a tissue site.

In some embodiments, the dressing 102 may also include a fluid interface, such as the connector 118, configured to fluidly couple the irrigation valve 116 to the sealed therapeutic environment formed by the cover 108. In some embodiments, the fluid interface may include a flange portion configured to couple the connector 118 to the cover 108. In other exemplary embodiments, a tube may be inserted through the cover 108 without the connector 118. Such a fluid interface can allow fluid to be delivered to the sealed therapeutic environment. For example, a fluid interface can provide a fluid conductor through the cover 108 to the tissue interface 110. In some embodiments, a fluid interface can also provide more than one fluid path through the cover 108 or merge more than fluid conductor into a single fluid path.

Irrigation therapy may provide a continuous or near continuous supply of fluids to a tissue site. The fluids may flow across a tissue site and remove undesired products of the healing process. For example, irrigation therapy may help remove necrotic tissue, bacteria, exudates, dirt, or other substances from the tissue site. Generally, saline may be used as an irrigation fluid. Saline can provide good infection control, and if appropriate, additional fluids may be added to the saline or may be provided in combination with saline to address specific issues of a particular tissue site.

Irrigation therapy does not generally include a dwell time; instead, fluids are preferably moved across the tissue site continuously. Continuous movement of fluid can use a large amount of fluid and can require frequent changing of waste fluid containers. Irrigation therapy may also require use of dedicated equipment, and systems for providing irrigation therapy may not interact well with other therapy systems. For example, an irrigation therapy system may require a positive-pressure pump to move irrigation fluid to and across a tissue site. If irrigation therapy is paired with negative-pressure therapy, operation of the positive-pressure pump can interfere with negative-pressure therapy if not managed properly. A clinician may be required to closely monitor the operation of both systems to ensure that both therapies are properly provided. The need for dedicated irrigation therapy equipment can also prove problematic in mobile situations, such as in emergency medical vehicles or small trauma centers. Space may be at a premium and many users may choose to only provide one type of therapy device. Consequently, many patients may not receive beneficial irrigation therapy.

The therapy system 100 can significantly decrease the cost and complexity of integrating irrigation therapy with negative-pressure therapy. In some embodiments, the therapy system 100 can enable a negative-pressure source to drive irrigation fluids, and permit the control of irrigation without interfering with negative-pressure therapy.

For example, in some embodiments, the negative-pressure can actuate the irrigation valve 116, drawing fluid through the irrigation valve 116 and to the tissue site. By using the therapy system 100 to actuate irrigation therapy, the rate at which fluids can be provided to a tissue site may be controlled by the application of negative-pressure. Furthermore, the irrigation valve 116 can provide irrigation therapy without requiring additional supplemental devices, such as a dedicated irrigation pump.

Figure 2A:
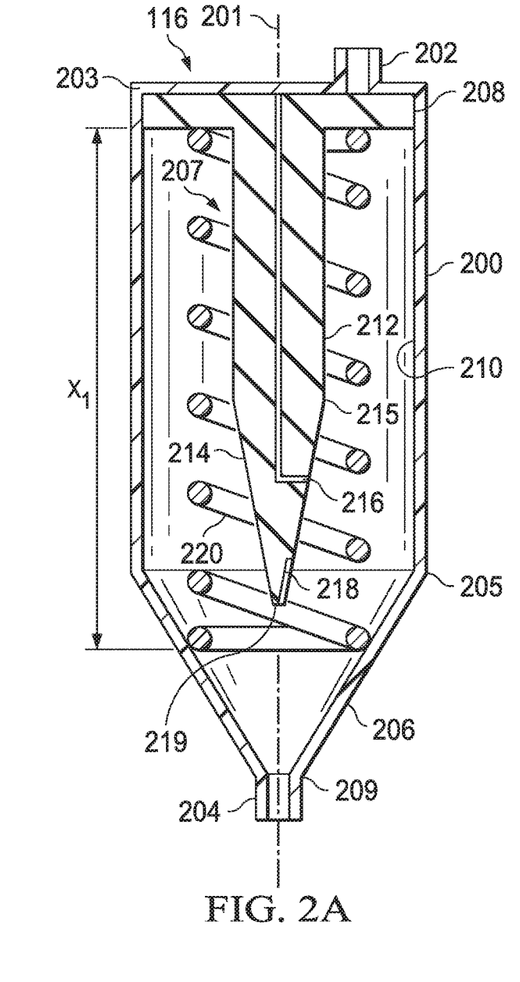
FIG. 2A is a schematic sectional view illustrating additional details that may be associated with an example embodiment of an irrigation valve of the therapy system 100 of FIG. 1.

FIG. 2A is a schematic sectional view illustrating additional details that may be associated with some example embodiments of the irrigation valve 116. In some embodiments, the irrigation valve 116 may include a valve body, such as a housing 200. The housing 200 may be tubular. In some embodiments, the housing 200 may form a portion of an exterior of the irrigation valve 116. If the housing 200 is tubular, the housing 200 may be an annular wall having an interior. In some embodiments, the housing 200 may have an axis 201.

In some embodiments, the irrigation valve 116 may include an end wall 203 and a conical end 206. The end wall 203 may be coupled to an end of the housing 200 and may close the end of the housing 200. The end wall 203 may prevent fluid communication through the end of the housing 200. The conical end 206 may be coupled to the housing 200 on an end that is opposite the end wall 203. In some embodiments, the conical end 206 may have a base 205 and an apex 209. The base 205 of the conical end 206 may be coupled to an end of the housing 200, and the conical end 206 may extend away from the housing 200 to the apex 209. In some embodiments, the conical end 206 may be coaxial with the axis 201. The end wall 203 and the conical end 206 may form boundaries of the interior of the housing 200. In some embodiments, the interior formed by the housing 200, the end wall 203, and the conical end 206 may be fluidly isolated from the ambient environment.

In some embodiments, the irrigation valve 116 may also include a valve inlet, such as a fluid inlet 202 and a valve outlet, such as a fluid outlet 204. The fluid inlet 202 may be coupled to the end wall 203. The fluid inlet 202 may be offset from the axis 201. For example, the fluid inlet 202 may be coupled to the end wall 203 radially outward from the axis 201 and proximate to the housing 200. In other embodiments, the fluid inlet 202 may be coaxial with the axis 201. In some embodiments, the fluid inlet 202 may be a fluid port or other device configured to allow fluid communication through the end wall 203. The fluid inlet 202 may be configured to be coupled to a fluid source, such as the fluid source 114, and to provide fluid communication between the fluid source and the interior of the housing 200. The fluid outlet 204 may be coupled to the apex 209 of the conical end 206 and may be coaxial with the axis 201. The fluid outlet 204 may be a fluid port or other device configured to allow fluid communication through the conical end 206. The fluid outlet 204 may be configured to be fluidly coupled to a sealed space adjacent a tissue site or to a negative-pressure source, such as the negative-pressure source 104.

In some embodiments, the irrigation valve 116 may include a plunger or piston, such as a piston 207. The piston 207 may be disposed in the interior of the housing 200 and form a first chamber, such as an outlet chamber or fluid outlet chamber 210. The piston 207 may have a cap, such as a head 208, a plunger rod or piston rod, such as a rod 212, and a plug or valve member 214. The head 208 may be a disc having an outer diameter substantially equal to an inner diameter of the housing 200. In some embodiments, one or more o-rings, piston rings, or sealing rings may be disposed around the head 208 to seal the head 208 to the housing 200. The head 208 may have a first surface facing the end wall 203 and a second surface facing toward the conical end 206. In some embodiments, the head 208 may reciprocate within the housing 200. For example, the head 208 may be in contact with the end wall 203 in a first position, as shown in FIG. 2A. In some embodiments, the head 208 may prevent fluid communication through the fluid inlet 202 if the head 208 is in contact with the end wall 203.

The rod 212 may be coupled to the head 208. In some embodiments, the rod 212 may be a cylinder and be coaxial with the axis 201. The rod 212 may have a first end coupled to the head 208 and extend from the head 208 toward the conical end 206. A second end of the rod 212 may be opposite the head 208. In other embodiments, the rod 212 may not be a cylinder and may not be coaxial with the axis 201.

The valve member 214 may be coupled to the second end of the rod 212. The valve member 214 may be a cone having a base 215 coupled to the rod 212 and extend away from the second end of the rod 212 to an apex 219. In some embodiments, a diameter of the base 215 of the valve member 214 may be substantially equal to a diameter of the rod 212. In some embodiments, the valve member 214 may be coaxial with the axis 201 and may have a length parallel to the axis 201.

In some embodiments, a bore or passage, such as a piston passage 216, may extend through the piston 207. For example, the piston passage 216 may pass through the head 208, extend through the rod 212, and terminate proximate to a side of the valve member 214. In some embodiments, the piston passage 216 may be coaxial with the axis 201 through the head 208. The piston passage 216 may remain coaxial with the axis 201 through the rod 212. In some embodiments, a portion of the piston passage 216 may be coaxial with the axis 201 through at least a portion of the valve member 214. The piston passage 216 may include an elbow that turns the piston passage 216 away from the axis 201. For example, as shown in FIG. 2A, the piston passage 216 may include an elbow that turns the piston passage 216 toward a side of the valve member 214 that connects the base 215 of the valve member 214 with the apex 219 of the valve member 214. In some embodiments, the piston passage 216 may terminate proximate to the base 215 of the valve member 214. In other embodiments, the piston passage 216 may not be coaxial with the axis 201. For example, the piston passage 216 may be located radially outward from the axis 201 at a location of the head 208 having a larger diameter than the outer diameter of the rod 212. In some embodiments, the piston passage 216 may not include an elbow, but may extend through the piston 207 at an angle.

The piston passage 216 may be separated or offset from the fluid inlet 202. For example, if the piston passage 216 is coaxial with the axis 201, the fluid inlet 202 may be positioned in the end wall 203 so that the fluid inlet 202 is not coaxial with the axis 201. In another example, if the fluid inlet 202 is coaxial with the axis 201, the piston passage 216 may be positioned to be radially separated from the axis 201. In some embodiments, if the head 208 of the piston 207 is in contact with the end wall 203, the piston passage 216 may not be in fluid communication with the fluid inlet 202. In some embodiments, the piston passage 216 may be sized to accommodate a particular flow rate at a particular pressure. In some embodiments, the piston passage 216 may be sized to accommodate a flow rate of about 10 cubic centimeters (cc)/minute when a pressure differential between the ends of the piston passage 216 is about 75 millimeters of mercury (mm Hg). In some embodiments, the piston passage 216 may have a diameter between about 1 millimeter (mm) and about 2 mm.

Figure 2B:
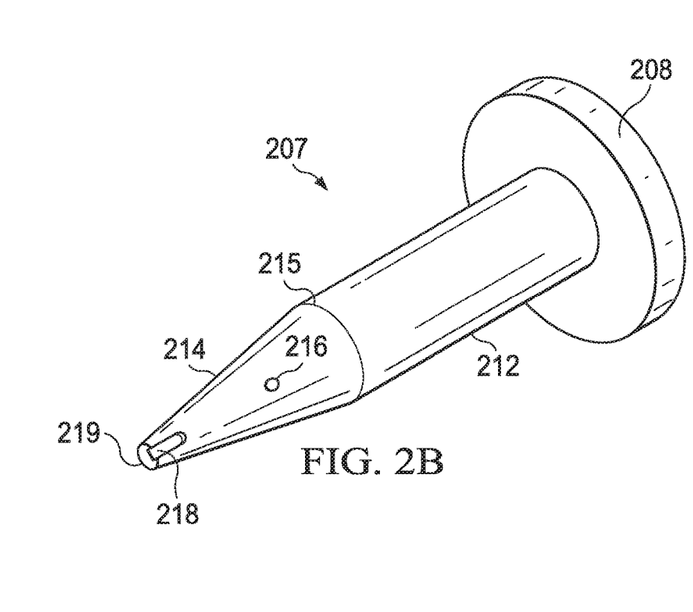
FIG. 2B is a perspective view illustrating additional details that may be associated with an example embodiment of a piston of the irrigation valve of FIG. 2A.

FIG. 2B is a perspective view illustrating additional details of an example embodiment of the piston 207. In some embodiments, another fluid passage, such as a groove 218, may be formed in the valve member 214. The groove 218 may extend from the apex 219 of the valve member 214 toward the base 215 of the valve member 214. In some embodiments, the groove 218 may have a length that is less than the length between the apex 219 and the base 215 of the valve member 214. As shown in FIG. 2B, the piston passage 216 may terminate in a side of the valve member 214.

Referring to FIG. 2A, the fluid outlet chamber 210 may be a variable volume chamber disposed in the interior of the housing 200. In some embodiments, the housing 200 may define a portion of the fluid outlet chamber 210. The fluid outlet chamber 210 may extend from the head 208 to the fluid outlet 204. In some embodiments, the fluid outlet chamber 210 may be coextensive with the interior of the housing 200. For example, if the head 208 is in contact with the end wall 203, the fluid outlet chamber 210 may be coextensive with the interior of the housing 200 between the head 208 and the fluid outlet 204. If the head 208 moves from contact with the end wall 203, the volume of the fluid outlet chamber 210 may change in response.

In some embodiments, the irrigation valve 116 may include a biasing member, such as a spring 220. The spring 220 may be disposed in the fluid outlet chamber 210 of the housing 200 between the second surface of the head 208 and the conical end 206. In some embodiments, the spring 220 may have a first end proximate to the conical end 206. A second end of the spring 220 may be adjacent to the head 208. In some embodiments, the rod 212 may be inserted into a center of the spring 220, and the spring 220 may at least partially circumscribe the rod 212. In some embodiments, the spring 220 may be coaxial with the axis 201.

As shown in FIG. 1, the irrigation valve 116 may be fluidly coupled to a fluid source 114 and a negative-pressure source 104 through a dressing 102. Referring to FIG. 2A, the fluid source 114 may be fluidly coupled to the fluid inlet 202. In some embodiments, the fluid in the fluid source 114 may exert a fluid pressure on the piston 207 through the fluid inlet 202. For example, the fluid source 114 may be positioned at a vertically higher elevation than the irrigation valve 116 and exert a fluid pressure on the piston 207 through the fluid inlet 202 due to the force of gravity. The fluid pressure may urge the head 208 toward the conical end 206. In other embodiments, the fluid pressure exerted by the fluid in the fluid source 114 may be negligible.

In some embodiments, the fluid outlet 204 may be fluidly coupled to a negative-pressure source, such as the negative-pressure source 104. If fluid is drawn from the fluid outlet chamber 210 through the fluid outlet 204, such as by operation of the negative-pressure source 104, a negative pressure may be developed in the fluid outlet chamber 210. The negative-pressure in the fluid outlet chamber 210 may generate a cause a differential pressure across the head 208 that exerts a force on the head 208 that urges the head 208 toward the conical end 206. The force of negative-pressure in the fluid outlet chamber 210 and fluid pressure through the fluid inlet 202 may be referred to as a differential force.

As shown in FIG. 2A, the irrigation valve 116 may be in a first position or a closed position. The head 208 may be in contact with the end wall 203, preventing fluid communication into the interior of the housing 200 through the fluid inlet 202. The differential force may urge the head 208 toward the conical end 206; however, the differential force may be insufficient to overcome the spring force of the spring 220. Generally, a spring, such as the spring 220 may exert a force that is proportional to a distance the spring is moved from a relaxed position. In some embodiments, the spring 220 may have a length $X_1$ if the irrigation valve 116 is in the closed position.

Figure 3:
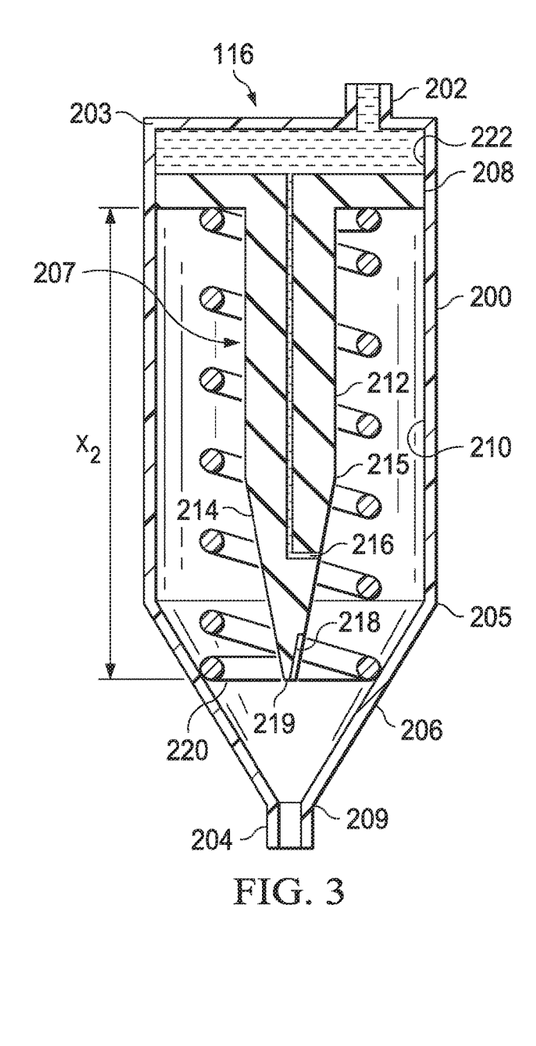
FIG. 3 is a schematic sectional view illustrating additional details of the irrigation valve of FIG. 2A in a high-flow position.

FIG. 3 is a schematic sectional view illustrating additional details that may be associated with some embodiments of the irrigation valve 116. As shown in FIG. 3, the irrigation valve is in a second position. The second position may also be referred to as an open position, a full fluid flow position, or a high flow position. In the high flow position, the differential force may exceed the spring force of the spring 220, and the head 208 may move toward the conical end 206. As the head 208 moves toward the conical end 206, a second chamber or inlet chamber, such as a fluid inlet chamber 222, may be formed in the housing 200. The fluid inlet chamber 222 may be bounded by the head 208, the end wall 203 and the housing 200. In some embodiments, the fluid inlet chamber 222 may form a portion of the interior of the housing 200. The fluid inlet chamber 222 may extend from the head 208 to the end wall 203. The fluid inlet chamber 222 may be in fluid communication with the fluid inlet 202 and the piston passage 216. Fluid entering the fluid inlet 202 may flow through the fluid inlet chamber 222 to the piston passage 216. In some embodiments, the fluid may flow through the piston passage 216 to the fluid outlet chamber 210. Fluid may then flow from the fluid outlet chamber 210 through the fluid outlet 204 and to a tissue site.

Generally, the flow rate through the piston passage 216 may be based in part on the negative pressure developed in the fluid outlet chamber 210. For example, the piston passage 216 may have a diameter between about 1 mm and about 2 mm and permit fluid flow at about 10 cubic centimeters/minute (cc/minute) if a negative pressure of about 75 mm Hg is developed in the fluid outlet chamber 210. In other embodiments, the diameter of the piston passage 216 may be varied to increase or decrease the fluid rate as needed for a given pressure.

Movement of the head 208 toward the conical end 206 may also compress the spring 220. For example, the spring 220 may be compressed from the length $X_1$ to a length $X_2$ that is less than the length $X_1$. If the negative pressure in the fluid outlet chamber 210 is decreased, for example, if the dressing 102 is removed from the tissue site, the spring 220 may exert a force on the head 208 that urges the head 208 toward the end wall 203. In some embodiments, the spring 220 may urge the head 208 into contact with the end wall 203 if the negative pressure decreases below about 65 mm Hg, preventing fluid communication through the fluid inlet 202.

Figure 4:
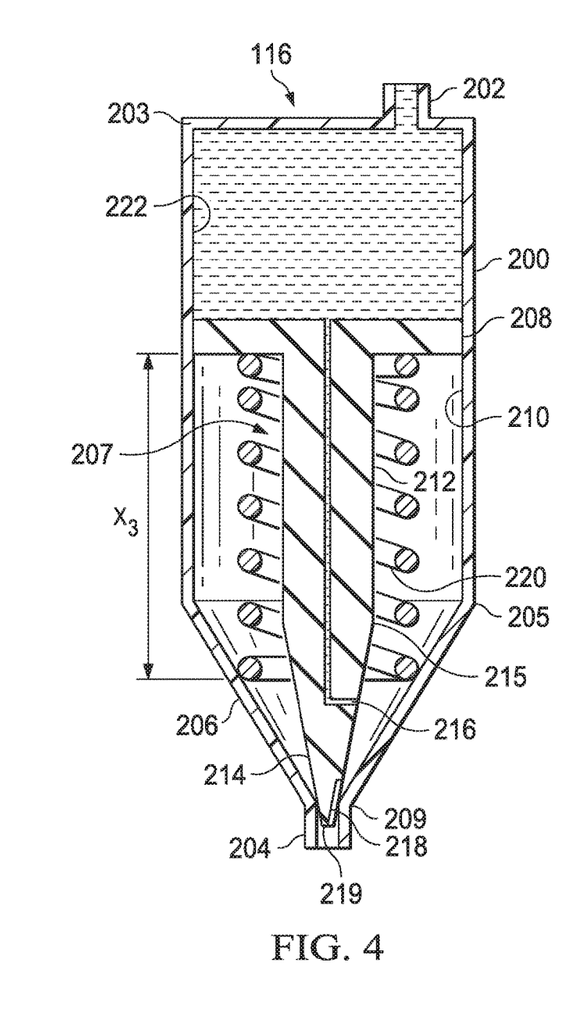
FIG. 4 is a schematic sectional view illustrating additional details of the irrigation valve of FIG. 2A is a low-flow position.

FIG. 4 is a schematic sectional view illustrating additional details that may be associated with some embodiments of the irrigation valve 116. As shown in FIG. 4, the piston 207 is in a third position, which may also be referred to as a low flow position. In some embodiments, the negative pressure developed in the fluid outlet chamber 210 may further compress the spring 220 between the head 208 and the conical end 206. As shown in FIG. 4, the spring 220 may be compressed to have a length $X_3$ that is less than the length $X_2$. In some embodiments, movement of the head 208 may move the valve member 214, coupled to the head 208 through the rod 212, into the fluid outlet 204. Positioning of the valve member 214 into the fluid outlet 204 may partially block fluid flow through the fluid outlet 204. In some embodiments, if the valve member 214 is in a seated position in the fluid outlet 204, the groove 218 may have a length sufficient to provide a fluid path through the fluid outlet 204. In some embodiments, the groove 218 may have a diameter between about 0.2 mm and about 0.3 mm Fluid may flow through the groove 218 at about 0.5 cc/minute when a reduced pressure of about 125 mm Hg is developed in the fluid outlet chamber 210.

In some embodiments, the irrigation valve 116 may be actuated by the negative-pressure source 104 to provide irrigation therapy. The negative-pressure source 104 may be turned on and set to provide an intermittent therapy. The negative-pressure source 104 may remove fluid from the tissue site to develop and maintain the negative pressure at the tissue site at about 125 mm Hg. During this time, the negative pressure developed at the tissue site may be communicated to the fluid outlet chamber 210 through the fluid outlet 204. In response, the piston 207 may move to the low flow position of FIG. 4. Fluid flow through the groove 218 and the fluid outlet 204 to the tissue site may be about 0.5 cc/minute. In some embodiments, the negative-pressure source 104 may maintain the negative pressure at about 125 mm Hg for about 60 minutes, providing about 30 cubic centimeters (cc) of fluid to the tissue site.

In some embodiments, the negative-pressure source 104 may stop developing negative-pressure for about 10 minutes. During this time period, the negative pressure at the tissue site and the fluidly coupled fluid outlet chamber 210 may decrease. In response, the spring 220, compressed to the length $X_3$, may exert a force on the head 208 of the piston 207, moving the head 208 toward the end wall 203 and removing the valve member 214 from the fluid outlet 204. Fluid may flow into the tissue site at about 10 cc/minute, providing about 100 cc of fluid to the tissue site.

If the pressure at the tissue site, or the fluid outlet 204 is at ambient pressure, for example, if the dressing 102 is removed from the tissue site, or if there is a leak preventing the development of negative pressure at the tissue site. The spring 220, compressed from the length $X_1$ to either the length of $X_2$ in FIG. 3 or $X_3$ in FIG. 4, may move the head 208 back into contact with the end wall 203, preventing fluid flow through the fluid inlet 202.

The negative-pressure source 104 and the irrigation valve 116 cooperate to provide continual flow of irrigation fluid through the irrigation valve 116 to the tissue site throughout the high-flow state of FIG. 3 and the low-flow state of FIG. 4. The negative-pressure developed by the negative-pressure source 104 interacts with the irrigation valve 116 and the groove 218 and piston passage 216 of the piston 207 to provide a continual flow of irrigation fluid.

The systems, apparatuses, and methods described herein may provide significant advantages. For example, the irrigation valve 116 may permit the application of an irrigation fluid to a wound from a simple, potentially disposable device, using existing vacuum therapy systems. The irrigation valve may also be used in the home and in emerging markets with little oversight. The irrigation valve may also be used with existing negative-pressure therapy system and devices without requiring a dedicated irrigation therapy pump.

The irrigation valve can provide controlled irrigation in a compact device. For example, the irrigation valve may be lightweight and sized to provide a known fluid flow for given conditions. A trauma center or emergency vehicle may have multiple irrigation valves sized to provide different flow rates at a same negative-pressure so that irrigation can be provided based on the needs of the tissue site. Furthermore, the irrigation valves may be made from materials that make disposal cost effective.

The irrigation valve may also be orientation insensitive. For example, the irrigation valve may operate as intended regardless of the position of the irrigation valve or the orientation of the irrigation valve relative to the force of gravity.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for irrigating a tissue site, comprising:
a tissue interface configured to be placed adjacent to the tissues site;
a sealing member configured to be placed over the tissue interface to form a sealed space;
a negative-pressure source configured to be fluidly coupled to the sealed space; and
an irrigation valve comprising:
a housing having a fluid inlet configured to be fluidly coupled to a fluid source and a fluid outlet configured to be fluidly coupled to the sealed space,
a piston disposed in the housing and forming a fluid inlet chamber fluidly coupled to the fluid inlet and a fluid outlet chamber fluidly coupled to the fluid outlet, the piston sealed to the housing to fluidly isolate the fluid inlet chamber from the fluid outlet chamber, wherein the piston comprises:
a cap comprising a first surface facing the fluid inlet, and a second surface facing the fluid outlet;
a piston rod comprising a proximal end and a distal end, the proximal end coupled to the second surface of the cap; and
a valve member coupled to the distal end and configured to engage the fluid outlet to at least partially prevent fluid flow through the fluid outlet;
a piston passage extending through the piston and fluidly coupling the fluid inlet chamber and the fluid outlet chamber, and
a biasing member coupled to the piston to bias the irrigation valve to a closed position;
wherein the negative-pressure source is configured to move the piston between the closed position and an open position to draw fluid to the sealed space.

2. The system of claim 1, wherein the valve member is conical.

3. The system of claim 2, further comprising a groove formed on a side wall of the valve member and configured to fluidly couple the fluid outlet to the fluid outlet chamber if the valve member is seated in the fluid outlet.

4. The system of claim 3, wherein the valve member has an axial length from an apex of the valve member to a base of the valve member and the groove extends a portion of the axial length.

5. The system of claim 3, wherein the groove has a diameter between about 0.2 mm and about 0.3 mm.

6. The system of claim 3, wherein the groove is sized to accommodate a flow rate of about 0.5 cc/minute at a negative pressure of about 125 mm Hg.

7. The system of claim 1, wherein the valve member forms a fluid passage fluidly coupling the fluid outlet to the fluid outlet chamber if the valve member is seated in the fluid outlet.

8. The system of claim 7, wherein the fluid passage has a diameter between about 0.2 mm and about 0.3 mm.

9. The system of claim 7, wherein the fluid passage is sized to accommodate a flow rate of about 0.5 cc/minute at a negative pressure of about 125 mm Hg.

10. The system of claim 1, wherein the piston passage is sized to accommodate a flow rate of about 10 cc/minute at a negative pressure of about 75 mm Hg.

11. The system of claim 1, wherein the piston passage has a diameter between about 1 mm to about 2 mm.

12. The system of claim 1, wherein the biasing member comprises a spring.

13. The system of claim 12, wherein the spring is disposed in the fluid outlet chamber, has a first end proximate to the fluid outlet, and a second end operatively coupled to the piston.

14. The system of claim 1, wherein the fluid source comprises saline.

15. The system of claim 1, wherein the fluid source comprises an intravenous fluid bag.

16. The system of claim 1, wherein the tissue interface comprises a manifold.

17. An irrigation valve, comprising:
a valve body comprising a valve inlet and a valve outlet, the valve body forming a chamber;
a plunger positioned in the chamber to form an inlet chamber in fluid communication with the valve inlet and an outlet chamber in fluid communication with the valve outlet, the plunger sealed to the valve body to fluidly isolate the inlet chamber from the outlet chamber, wherein the plunger comprises:
a head comprising a diameter, a first surface facing the valve inlet, and a second surface facing the valve outlet;
a rod extending from the second surface of the head and having a diameter less than the diameter of the head; and
a plug attached to the rod opposite the head, the plug configured to at least partially prevent fluid flow through the valve outlet in a seated position;
a bore extending through the plunger and in fluid communication with the inlet chamber and the outlet chamber; and a spring positioned to bias the plunger away from the valve outlet to a closed position.

18. The irrigation valve of claim 17, wherein the plug is conical.

19. The irrigation valve of claim 18, further comprising a groove formed on a side wall of the plug and configured to fluidly couple the valve outlet to the outlet chamber if the plug is seated in the valve outlet.

20. The irrigation valve of claim 19, wherein the groove extends a portion of an axial length of the plug from an apex of the plug a base of the plug.

21. The irrigation valve of claim 19, wherein the groove has a diameter between about 0.2 mm and about 0.3 mm.

22. The irrigation valve of claim 19, wherein the groove is sized to accommodate a flow rate of about 0.5 cc/minute at a negative pressure of about 125 mm Hg.

23. The irrigation valve of claim 17, wherein the plug forms a fluid passage fluidly coupling the valve outlet to the outlet chamber if the plug is seated in the valve outlet.

24. The irrigation valve of claim 23, wherein the fluid passage has a diameter between about 0.2 mm and about 0.3 mm.

25. The irrigation valve of claim 23, wherein the fluid passage is sized to accommodate a flow rate of about 0.5 cc/minute at a negative pressure of about 125 mm Hg.

26. The irrigation valve of claim 17, wherein the bore is sized to accommodate a flow rate of about 10 cc/minute at a negative pressure of about 75 mm Hg.

27. The irrigation valve of claim 17, wherein the bore has a diameter between about 1 mm to about 2 mm.

28. The irrigation valve of claim 17, wherein the spring is disposed in the outlet chamber, has a first end proximate to the valve outlet, and a second end operatively coupled to the plunger.

29. The irrigation valve of claim 17, wherein the valve inlet is configured to be coupled to a fluid source.

30. The irrigation valve of claim 17, wherein the valve outlet is configured to be coupled to a negative-pressure source.

31. A method for controlling irrigation of a tissue site, the method comprising:
    placing a tissue interface adjacent to the tissue site;
    covering the tissue interface and the tissue site to form a sealed space;
    fluidly coupling an irrigation valve to the sealed space;
    fluidly coupling a fluid source to the irrigation valve; and
    supplying negative pressure to the irrigation valve through the tissue interface to draw a piston of the irrigation valve toward a fluid outlet to open a fluid inlet fluidly coupled to a fluid inlet chamber of the irrigation valve and draw irrigation fluid to the tissue site through a fluid outlet chamber and the fluid outlet of the irrigation valve;
    wherein the piston is sealed to the irrigation valve to fluidly isolate the fluid inlet chamber from the fluid outlet chamber; and
    wherein the piston comprises:
        a cap comprising a first surface facing the fluid inlet, and a second surface facing the fluid outlet;
        a piston rod comprising a proximal end and a distal end, the proximal end coupled to the second surface of the cap; and
        a valve member coupled to the distal end and configured to engage the fluid outlet to at least partially prevent fluid flow through the fluid outlet.

32. The method of claim 31, wherein fluidly coupling an irrigation valve to the sealed space comprises fluidly coupling the fluid outlet to the tissue interface.

33. The method of claim 31, wherein fluidly coupling a fluid source to the irrigation valve comprises fluidly coupling a fluid source to the fluid inlet.

34. The method of claim 31, wherein supplying negative pressure comprises supplying negative pressure at about 75 mm Hg to move the irrigation valve to a high-flow position and draw the irrigation fluid through the fluid outlet at about 10 cc/minute.

35. The method of claim 31, wherein supplying negative pressure comprises supplying negative pressure at about 125 mm Hg to move the irrigation valve to a low-flow position and draw the irrigation fluid through the fluid outlet at about 0.5 cc/minute.

36. A method for operating an irrigation valve, the method comprising:
    fluidly coupling a fluid source to a fluid inlet of the irrigation valve;
    fluidly coupling a negative-pressure source to a fluid outlet of the irrigation valve; and
    supplying negative pressure from the negative-pressure source to the fluid outlet of the irrigation valve;
    wherein the negative pressure draws a piston of the irrigation valve toward the fluid outlet to open a fluid inlet of the irrigation valve and draws fluid through a fluid inlet chamber, a passage of the piston, a fluid outlet chamber, and the fluid outlet of the irrigation valve; and
    wherein the piston is sealed to the irrigation valve to fluidly isolate the fluid inlet chamber from the fluid outlet chamber; and
    wherein the piston comprises:
        a cap comprising a first surface facing the fluid inlet, and a second surface facing the fluid outlet;
        a piston rod comprising a proximal end and a distal end, the proximal end coupled to the second surface of the cap; and
        a valve member coupled to the distal end and configured to engage the fluid outlet to at least partially prevent fluid flow through the fluid outlet.

37. The method of claim 36, wherein the fluid outlet is formed in a housing of the irrigation valve.

38. The method of claim 36, wherein the fluid inlet is formed in a housing of the irrigation valve.

39. The method of claim 36, wherein:
    supplying negative pressure comprises supplying negative pressure at about 75 mm Hg; and
    the negative pressure moves the piston to a high flow position and draws fluid through the passage at about 10 cc/minute.

40. The method of claim 36, wherein:
    supplying negative pressure comprises supplying negative pressure at about 125 mm Hg; and
    the negative pressure moves the piston to a low flow position and draws fluid through the passage at about 0.5 cc/minute.

* * * * *

UNITED STATES PATENT AND TRADEMARK OFFICE
CERTIFICATE OF CORRECTION

PATENT NO. : 11,083,884 B2
APPLICATION NO. : 15/580756
DATED : August 10, 2021
INVENTOR(S) : Tim Robinson Page 1 of 1

It is certified that error appears in the above-identified patent and that said Letters Patent is hereby corrected as shown below:

In the Claims

<u>Column 15</u>
Line 11 Claim 20, between "of the plug" and "a base" insert -- to --, therefor.

Signed and Sealed this
Seventh Day of May, 2024

Katherine Kelly Vidal
*Director of the United States Patent and Trademark Office*